United States Patent

Schalkhammer et al.

[11] Patent Number: 5,866,433
[45] Date of Patent: Feb. 2, 1999

[54] OPTOCHEMICAL FLUORESCENCE SENSOR AND METHOD FOR MEASURING THE CONCENTRATION OF AT LEAST ONE ANALYTE IN A SAMPLE

[75] Inventors: Thomas Schalkhammer, Kasten; Fritz Pittner, Wien; Alfred Leitner, Graz; Franz Aussenegg, Graz; Harald Brunner, Graz, all of Austria

[73] Assignee: AVL Medical Instruments AG, Schaffhausen, Switzerland

[21] Appl. No.: 616,153

[22] Filed: Mar. 14, 1996

[30] Foreign Application Priority Data

Mar. 17, 1995 [AT] Austria .................................. A 474/95

[51] Int. Cl.[6] .................................................. G01N 33/553
[52] U.S. Cl. .......................... 436/525; 422/57; 422/82.05; 422/82.08; 422/82.11; 435/6; 435/287.1; 435/287.2; 435/287.9; 435/288.7; 435/808; 436/518; 436/524; 436/527; 436/164; 436/165; 436/172; 436/805; 436/807; 385/12; 385/129; 385/131
[58] Field of Search ..................... 422/57, 82.05, 422/82.08, 82.11; 435/6, 287.1, 287.2, 287.9, 288.7, 808; 436/518, 524, 525, 527, 164, 165, 172, 800, 805, 807; 385/12, 129, 131

[56] References Cited

U.S. PATENT DOCUMENTS 4,978,503  12/1990  Shanks et al. ............................. 422/58
5,449,918   9/1995  Krull et al. .
5,527,712   6/1996  Sheehy .................................... 436/525

FOREIGN PATENT DOCUMENTS 4210970  10/1993  Germany .
2243683  11/1991  United Kingdom .

Primary Examiner—Christopher L. Chin
Attorney, Agent, or Firm—Watson Cole Grindle Watson, P.L.L.C.

[57] ABSTRACT

An optochemical fluorescence sensor with a biorecognitive layer for measuring the concentration of one or more analytes in a sample is provided with at least one island layer which is applied on a sensor substrate. The islands of the island layer are in the form of electrically-conductive material and have a diameter of less than 300 nm, the biorecognitive layer being directly applied on the island layer or bound via a spacer film. In addition, an analyte-specific fluorescent compound is provided which may be added to the sample or is provided in the sensor itself. The biorecognitive layer can bind the analyte to be measured directly or by means of analyte-binding molecules, the originally low quantum yield of the fluorescent compound increasing strongly in the vicinity of the island layer.

18 Claims, 4 Drawing Sheets

OPTOCHEMICAL FLUORESCENCE SENSOR AND METHOD FOR MEASURING THE CONCENTRATION OF AT LEAST ONE ANALYTE IN A SAMPLE

BACKGROUND OF THE INVENTION

This invention relates to an optochemical fluorescence sensor with a biorecognitive layer and to a method for measuring the concentration of one or more analytes in a sample.

Optochemical sensors are based on the fact that a chemical reaction between the sensor material and the analyte leads to a change in the optical properties of the sensor. Such a change may concern optical properties such as absorption or fluorescence intensity; as a consequence, the reaction may be detected by means of spectroscopic methods.

Optochemical sensors for measuring concentrations of chemical substances meet with growing interest for several reasons; compared to conventional measuring devices they feature shorter response times, greater mechanical robustness and insensitivity to electromagnetic interferences, in addition to other advantages. To ensure short response times, however, it is essential for such optochemical sensors that the sensor material be sufficiently exposed to the attack of the analyte.

DESCRIPTION OF THE PRIOR ART

In GB-A 2,243,683 an optochemical sensor is described in which a biorecognitive layer is provided on the end of a fiber optic, which layer is able to contact an analyte contained in a sample. The biorecognitive layer exhibits fluorescence-labeled antigens bound to antibodies, which antigens are replaced by the analyte upon contact with the sample. The decrease in fluorescence is detected as a measure for the analyte concentration.

Publication DE-A1 42 10 970 is concerned with a method for optical qualitative and quantitative detection of biomolecules, toxic substances, polymers and pharmaceutical agents with the use of laser spectroscopy. In this method fluorescent dyes are coupled to the target molecules and detected via the fluorescence decay time which is not affected by the labeled molecule. Among the fluorescent dyes used in this context are fluoresceins and rhodamines.

SUMMARY OF THE INVENTION

It is an object of the invention to provide an optochemical sensor of the above kind which will permit the concentrations of analytes, such as antibodies or enzymes, to be determined in a simple and reproducible manner, where no electrodes are needed and the measured result may be obtained rapidly and most accurately, even if the changes in the concentration to be measured are minute.

In the invention this object is achieved by proposing that the sensor be provided with at least one island layer applied on a substrate, the islands of the layer consisting of electrically-conductive material and having a diameter of smaller than 300 nm, and the biorecognitive layer being applied to the island layer or bound thereto via a spacer film, and that an analyte-specific fluorescent compound be provided for addition to the sample or as part of the sensor, and further that the biorecognitive layer be capable of binding the analyte to be measured directly or by means of analyte-binding molecules, the quantum yield of the fluorescent system being small and increasing strongly in the vicinity of the island layer.

A sensor of the invention thus essentially comprises;
(1) a layer consisting of a plurality of nanometric particles (=islands) of electrically-conductive material, in particular, metal, which is applied to the surface of a substrate,
(2) a biorecognitive layer on or above the island layer,
(3) biorecognitive molecules which are labeled with weak or moderately strong fluorophors, the diameter of the islands being smaller than the wavelength of the light utilized for monitoring and evaluation.

A method of the invention for measuring the concentration of at least one analyte in a sample thus comprises the steps of;
(a) contacting the sample with a biorecognitive sensor layer which is applied on or in close vicinity of at least one island layer consisting of islands of electrically conductive material,
(b) contacting the sample with an analyte-specific fluorescent compound of low quantum yield,
(c) binding the analyte-specific fluorescent compound to the analyte, which in turn is bound by the biorecognitive layer, the quantum yield of the analyte-specific fluorescent compound increasing strongly in the vicinity of the island layer,
(d) radiating excitation radiation which is suitable for excitation of the analyte-specific fluorescent compound into the at least one island layer,
(e) determining the fluorescence radiation emitted by the bound analyte-specific fluorescent compound as a measure for the analyte concentration.

As an alternative to item (c), both the analyte-specific fluorescent compound and the analyte to be measured are bound by the biorecognitive layer, the quantum yield of the analyte-specific fluorescent compound again increasing strongly in the vicinity of the island layer.

It is proposed by the invention that the analyte-specific fluorescent compound be a fluorescence-labeled biorecognitive molecule which is able to bind the analyte, or that the analyte-specific fluorescent compound be a fluorescence-labeled analyte analogue which can be bound by the biorecognitive layer. In such a sensor the property of the biorecognitive layer above the island layer is utilized, either to bind the analyte and a fluorescence-labeled, analyte-detecting molecule bound thereto as a "molecular sandwich" upon contact with the analyte, or to bind an analyte after competitive displacement of the fluorescence-labeled analyte analogue by the analyte.

In an optochemical sensor of the invention such a biorecognitive bonding reaction will lead to a change in the optical sensor properties, above all to a strong increase in the quantum yield (fluorescence) of fluorophors in the range of 0–20 nm above the island layer.

In conventional fluorescence sensors fluorophors with a high quantum yield must be employed to guarantee the necessary sensitivity of the sensor. On the other hand dissolved fluorescent molecules in the sensor environment will produce a strong background signal limiting the sensitivity of the measuring system. To obtain a satisfactory signal-to-noise ratio, excess fluorophor solutes must be removed from the sensor prior to measurement. The new type of optochemical fluorescence sensor described by the invention does not have this disadvantage since the dissolved molecules exhibit a very low intrinsic fluorescence which will strongly increase only after bonding to the biorecognitive layer. As a consequence, the biorecognitive bond can be measured immediately and selectively at the surface of the sensor without separation of the analyte solution, which is not possible in conventional sensors.

It will thus be possible to observe a change in optical properties, such as fluorescence intensity or the fluorescence spectrum, after a comparatively short response time. It has been found unexpectedly that in such a structure the characteristic measuring effects will occur only in the region of energetic coupling (at a distance of less than 20 nm) of the optically active molecules (e.g., fluorophors) with the island layer. As with all other sensors, response time of the sensor is determined by the time it takes the substance to be measured to diffuse into the sensor material; by using extremely thin layers as proposed by the invention, a suitably short diffusion path can be provided. By means of conventional methods of interferometry or surface plasmon resonance, slight chemical changes in thin layers may be detected only with the use of complex measuring equipment. It has been found quite unexpectedly that a much simpler measuring configuration is obtained, in addition to greater sensor sensitivity, if the island layer is applied on a transparent surface and is used for coupling in the measuring beam (e.g., laser or LED).

Metallic island layers with an island diameter smaller than the wavelength of the light used for monitoring and evaluation are characterized by strong absorption, as a consequence of which the system described above exhibits a strong spectral reflection maximum. Fluorophors with an emission wavelength in the island spectrum, which originally have a small quantum yield, will strongly increase their efficiency if they are added to a thin layer of about 20 nm above the island layer.

In a preferred embodiment the islands of the island layer consist of gold or silver. Although other metals, such as aluminium, would also be suitable as an island layer, they are more easily susceptible to chemical attack than the preferred island layer of gold or silver. Moreover, gold and silver feature excellent absorption properties and thus a strong increase in quantum yield accompanied by high analyte sensitivity. Upon contact with the island layer a fluorophor will basically gain in quantum yield all the more the smaller its quantum yield is per se. In this respect the method proposed by the invention differs from all known fluorescence sensors, where the analyte sensitivity is proportial to the quantum yield of the respective fluorophor.

Due to the measuring geometry of the optical biosensor, the excitation light can be radiated into the transparent side of the sensor which is not in contact with the sample, and the emitted fluorescent photons may be measured at the maximum solid angle on the same side.

Suitable light sources are all thermal emitters, light-emitting diodes, and lasers (frequency doubled junction lasers); for photon measurement photomultiplers or photo-semiconductors (inferior detection limit) may be employed.

A particularly strong increase in fluorescence intensity is observed if the diameter of the islands is appreciably smaller than the wavelength of the light used for monitoring and evaluation, and if the absorption minimum overlaps with the emission maximum of the fluorophor. In a preferred embodiment the diameter of the islands is smaller than 100 nm, i.e., preferably smaller than 60 nm, if visible light is used for evaluation.

It is provided by the invention that the biorecognitive layer on or above the island layer consist of proteins, lipids, nucleic acids, or artificial ligands. In this context preference is given to proteins, such as antibodies, antigens, and lectines, as well as hormones, DNA, and RNA. Such biorecognitive systems exhibit selective binding of the analyte. It will suffice in this case if such a sensor is brought into contact with a solution whose concentration is to be determined.

The analyte-specific fluorescent compound may preferably be provided with proteins, such as antibodies, antigens and lectines, as well as hormones, lipids, DNA and RNA; these molecules are conjugated with a fluorophor, however. Such biorecognitive systems are also characterized by selective binding of the analyte; it will suffice to contact them with the analyte in dissolved form.

Due to the thinness of the layer and the short response time resulting therefrom, the increase in fluorescence intensity can be detected quickly and reliably. At the same time, the comparatively simple structure of the optochemical sensors will ensure a high degree of mechanical stability. To guarantee a sufficiently short response time in addition to an appreciable increase in the fluorescence intensity of the layer system, it is proposed in a preferred embodiment that the thickness of the immobilized biorecognitive layer be smaller than 20 nm, preferably smaller than 15 nm. To increase fluorescence yield the thickness should not be smaller than 3 to 5 nm, however; for practical purposes, layer thicknesses of 5 to 15 nm are best.

In order to maintain the high absorption desired by the invention along with good permeability for diffusion of the analyte, the proposal is put forward that an island layer of gold or silver, for example, have a thickness of less than 25 nm, i.e., preferably less than 15 nm, its light absorption preferably amounting to 40–60 percent for the particular wavelength used, to ensure especially high sensitivity.

The optochemical sensor described by the invention may be produced in a simple manner by slowly applying the island layer directly onto the substrate, using techniques such as vapor deposition, sputtering, or electron beam lithography. By vapor depositing the layer the extremely small mass thickness and the formation of discrete islands required by the invention are reliably obtained, which will result in the typical spectral properties of the system. As an alternative, the island layer may be produced or modified by the attachment of metallic particles or islands to the substrate, or by removing excess metal from the substrate layer, thereby forming islands or changing their number or size, in which way the desired mass thickness may be obtained accurately.

An optochemical sensor is conveniently prepared by immobilizing a biorecognitive layer directly on the island layer, or via a thin (less than 10 nm) intermediate layer or spacer film. In this way the analyte concentration may be immediately determined in situ via a biorecognitive bond, where at least one molecule of the fluorescence-labeled compound is bound per analyte molecule.

The biorecognitive layer and the analyte-specific fluorescent compound are conveniently reacted in one step on or above the sensor. In this context the use of at least one fluorophor from the group of fuchsines, erythrosines, rhodamines, or of similar molecules that are crosslinked with a biorecognitive molecule will be of advantage.

The islands may further be formed by the attachment of microcolloidal metallic particles.

In addition to the irreversible application of an optical sensor as described above, optochemical sensors are of interest which can be used repeatedly. Such optochemical sensors are able to exploit reversible chemical or biochemical bonding reactions, where the island layer of gold, for example, is coated with a semipermeable membrane which is permeable only to small analyte molecules.

Finally, a sensor modified in such manner may be employed to measure glucose, lactate, etc., by directly reacting the analyte and a competing fluorescent analyte analogue with the biorecognitive system.

BRIEF DESCRIPTION OF THE DRAWINGS

The invention will be further described with reference to the accompanying drawings, in which.

DETAILED DESCRIPTION OF PREFERRED EMBODIMENTS

Figure 1:
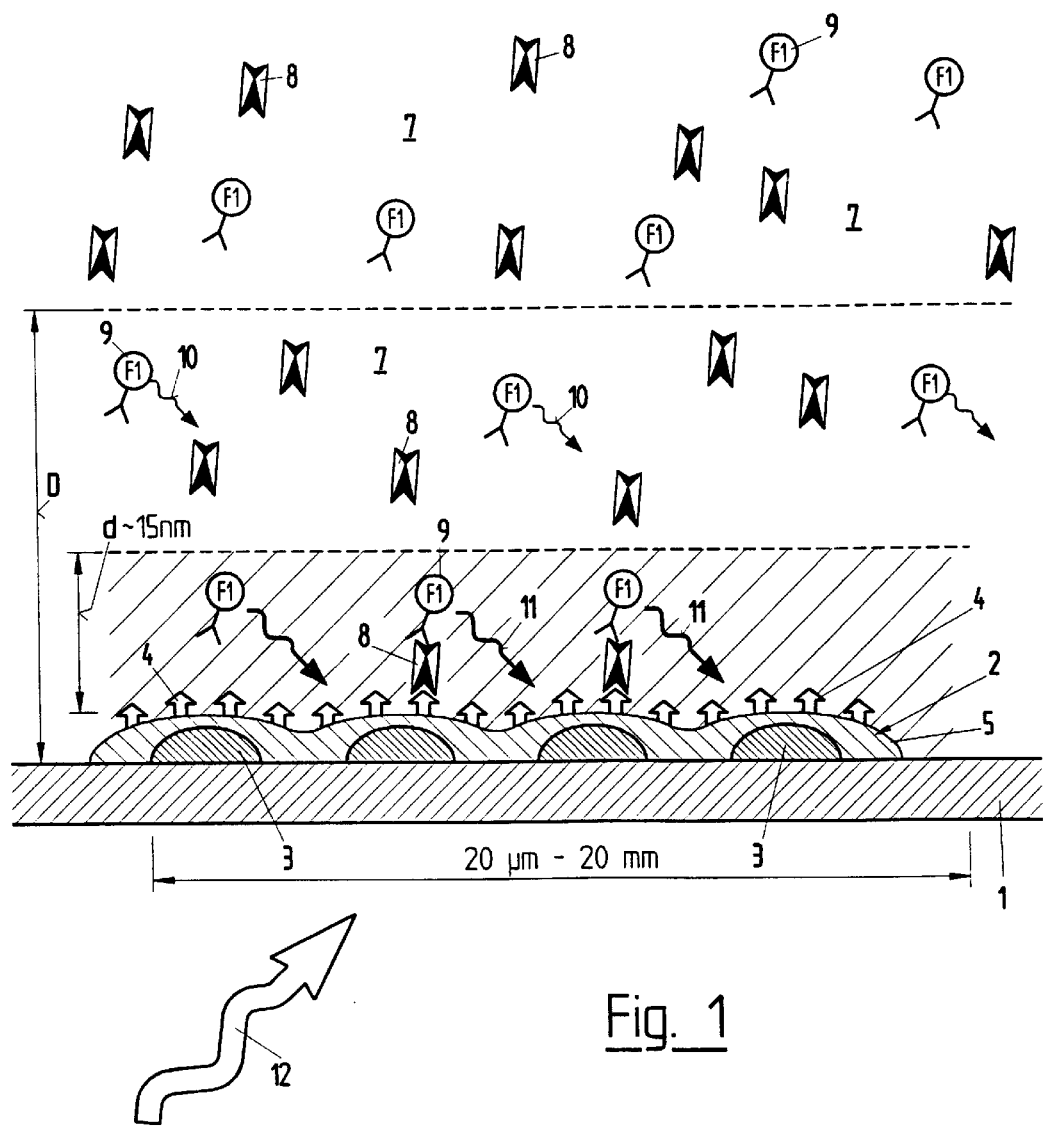
FIG. 1 is a schematical representation of a sensor described by the invention.

FIG. 1 shows an optochemical fluorescence sensor comprising a substrate 1 on which is applied an island layer 2 consisting of a plurality of electrically-conductive islands 3, which are preferably made of gold or silver. The islands 3 have a diameter of smaller than 300 nm and may be vapor-deposited on the substrate. A biorecognitive layer 4 is either applied directly to the island layer 2 or, as shown in FIG. 1, immobilized via a spacer film 5. The biorecognitive layer contacts a sample 7 either directly or via an analyte-permeable membrane 6 (see FIG. 4).

In addition to the analyte 8 the sample 7 is provided with an analyte-specific fluorescent compound 9, which is added to the sample 7 before the measuring process or is already provided in the sensor. In FIG. 1 the analyte-specific fluorescent compound 9 consists of a fluorescence-labeled biorecognitive molecule originally fluorescing with low quantum yield, i.e., less than 30% (cf. arrows 10). The biorecognitive molecule with fluorophor F1 is capable of coupling to the analyte 8, which in turn is bound by the biorecognitive layer 4 on the island layer 2. In the vicinity of the island layer 2, within a distance d of about 15 nm (region of fluorophor/island coupling) the quantum yield of the analyte-specific fluorescent compound 9 increases strongly. The increasing fluorescence radiation (arrow 11) is a function of the concentration of the analyte 8. Distance D indicates the penetration depth of the evanescent wave of the excitation radiation 12.

Figure 2:
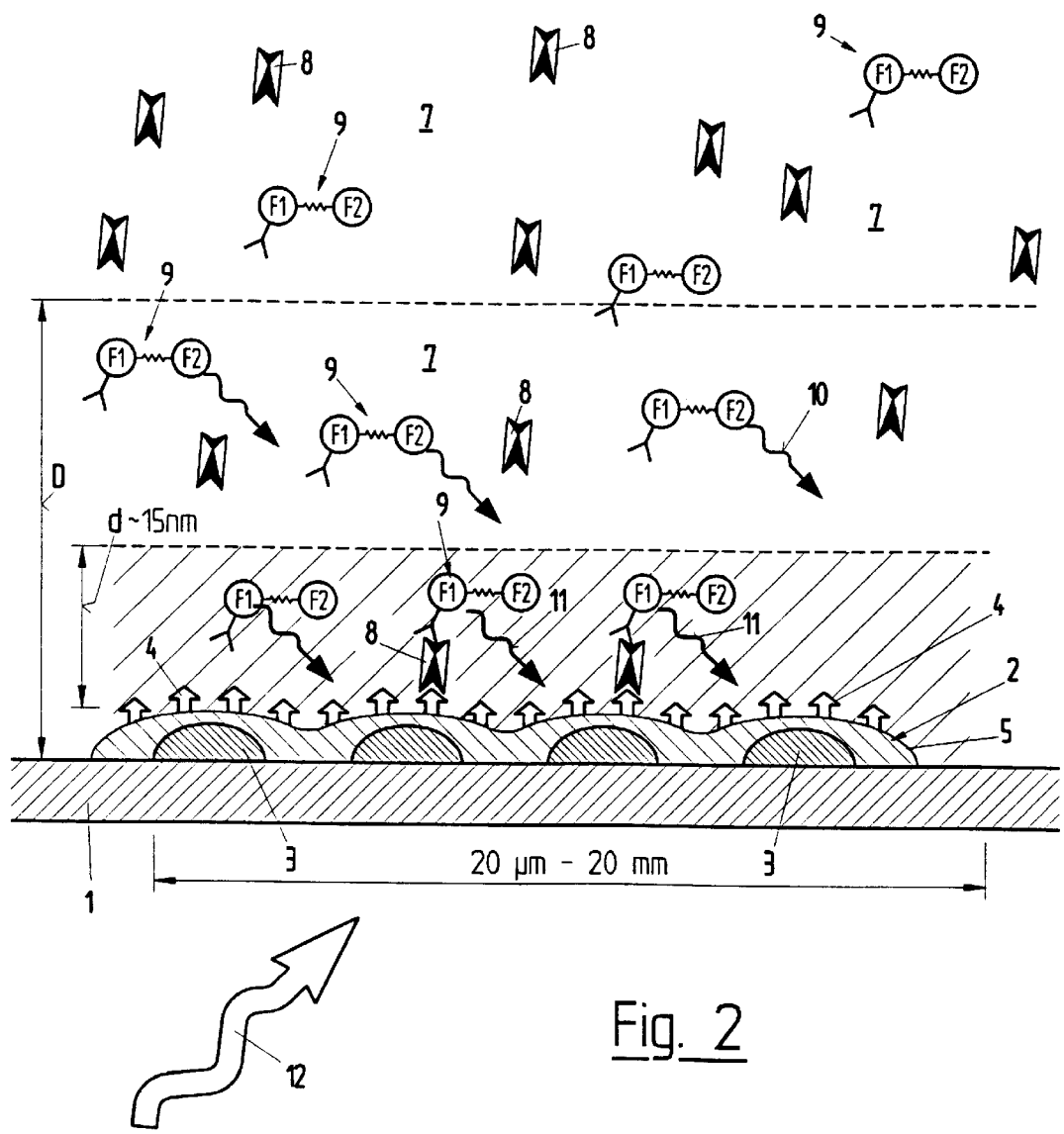
FIGS. 2 to 4 are variants of the above sensor.
Figure 3:
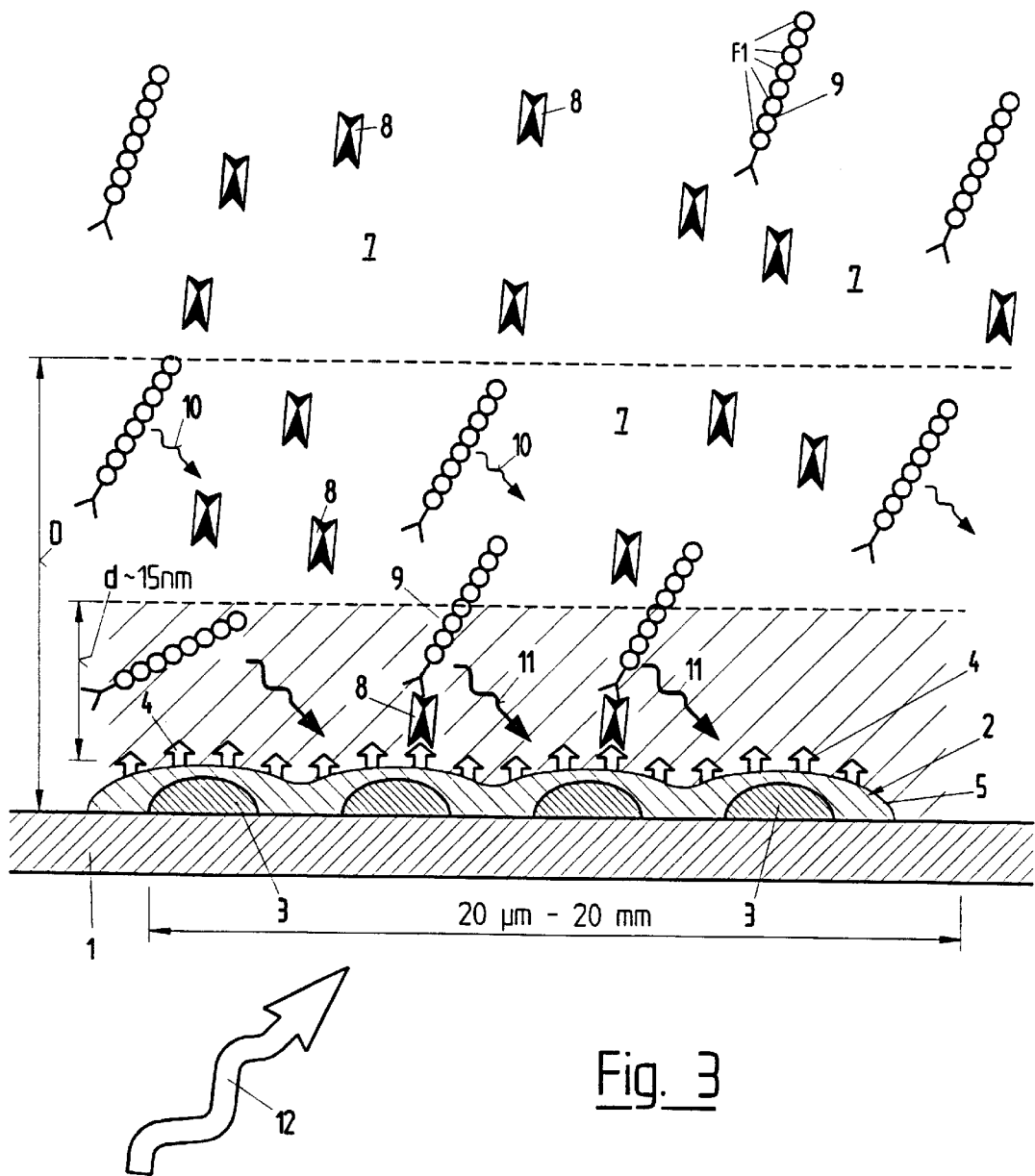
Figure 4:
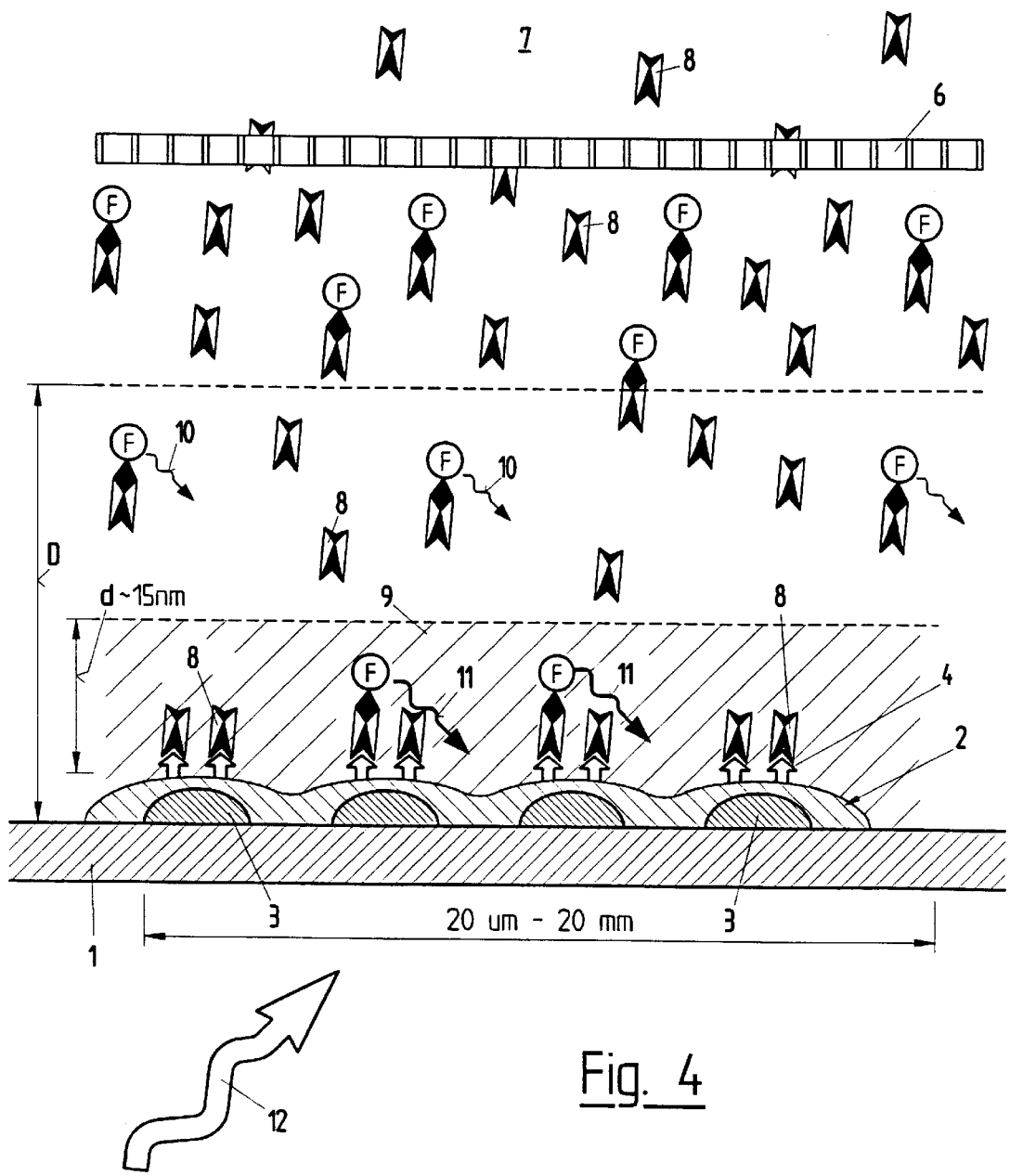

FIGS. 2 to 4 essentially show the same configuration as the fluorescence sensor presented in FIG. 1, the analyte-specific fluorescent compound 9 comprising two coupled fluorophors F1 and F2 in FIG. 2, for example. The quantum yield of the first fluorophor F1 is quenched by processes of energy transfer to the second fluorophor F2. In the vicinity of the island layer 2 the coupling between the two fluorophors is broken, leading to a strong increase in the intensity of the fluorescence radiation of the fluorophor F1 (cf. arrow 11). F2 could also be a non-fluorescent molecule quenching the fluorescence radiation of fluorophor F1.

In FIG. 3 the analyte-specific fluorescent compound 9 comprises a plurality of fluorophors F1, the spatial density of which leads to strong self-quenching effects. The self-quenching effects are cancelled within distance d (region of fluorophor/island coupling), which again will lead to an increase in the intensity of the fluorescence radiation.

FIG. 4 finally gives an example in which the analyte-specific fluorescent compound 9 consists of a fluorescence-labeled analyte analogue which competes with the analyte 8 in binding to the biorecognitive layer 4.

We claim:

1. A method for measuring the concentration of at least one analyte in a sample, comprising the steps of
   (a) contacting the sample with a biorecognitive sensor layer, which is applied on or in close vicinity of at least one island layer consisting of islands of electrically-conductive material,
   (b) contacting the sample with an analyte-specific fluorescent compound of low quantum yield,
   (c) binding the analyte-specific fluorescent compound to the analyte, which in turn is bound by the biorecognitive layer, the quantum yield of the analyte-specific fluorescent compound increasing strongly in the vicinity of the island layer,
   (d) radiating excitation radiation into the at least one island layer, which is suitable for excitation of the analyte-specific fluorescent compound,
   (e) determining the fluorescence radiation emitted by the bound analyte-specific fluorescent compound as a measure for the analyte concentration.

2. Method according to claim 1, wherein as an alternative to step (c) both the analyte-specific fluorescent compound and the analyte to be measured are bound by the biorecognitive layer, the quantum yield of the analyte-specific fluorescent system increasing strongly in the vicinity of the island layer.

3. A combination of an optochemical fluorescence measuring apparatus and an analyte-specific fluorescent compound for measuring the concentration of an analyte in a sample,
   said optochemical fluorescence measuring sensor comprising a substrate, an island layer consisting of islands of electrically-conductive material on the substrate, said islands having a diameter of less than 300 nm; a biorecognitive layer applied to said island layer; said biorecognitive layer being capable of binding with said analyte; and
   said analyte-specific fluorescent compound having a quantum yield which increases strongly in the vicinity of said island layer.

4. A sensor according to claim 3, wherein said analyte-specific fluorescent compound is a fluorescence-labeled biorecognitive molecule which is able to bind said analyte.

5. A sensor according to claim 4, wherein said analyte-specific fluorescent compound includes a fluorophor having a quantum yield of less than 30%.

6. A sensor according to claim 4, wherein said analyte-specific fluorescent compound comprises two coupled molecules, at least one of which is a fluorophor whose quantum yield is reduced by spatial vicinity to the other molecule quenching the fluorescence of said fluorophor.

7. A sensor according to claim 6, wherein said fluorophor is a fluorescein or a rhodamine.

8. A sensor according to claim 4, wherein the molecules of said fluorophor of said analyte-specific fluorescent compound have a spatial density which leads to strong self-quenching.

9. A sensor according to claim 8, wherein said fluorophor is a fluorescein.

10. A sensor according to claim 3, wherein said analyte-specific fluorescent compound is a fluorescence-labeled analyte analogue which can be bound by said biorecognitive layer.

11. A sensor according to claim 10, wherein said fluorophor of said analyte-specific fluorescent compound has a quantum yield of less than 30%.

12. A sensor according to claim 10, wherein said analyte-specific fluorescent compound comprises two coupled molecules, at least one of which is a fluorophor whose quantum yield is reduced by spatial vicinity to the other molecule quenching the fluorescence of said fluorophor.

13. A sensor according to claim 10, wherein the molecules of said fluorophor of said analyte-specific fluorescent compound have a spatial density which leads to strong self-quenching.

14. A sensor according to claim 3, wherein said islands of said island layer are made of gold or silver.

15. A sensor according to claim 14, wherein the diameter of said islands is smaller than 100 nm.

16. A sensor according to claim 3, wherein the biorecognitive layer on or above said island layer consists of proteins, lipids, nucleic acids, or artificial ligands.

17. A sensor according to claim 3, wherein said island layer has a thickness of less than 25 nm.

18. A sensor according to claim 3, wherein said analyte-specific fluorescent compound contains at least one fluorophor from a group consisting of fuchsines, erythrosines and rhodamines.

* * * * *

UNITED STATES PATENT AND TRADEMARK OFFICE
CERTIFICATE OF CORRECTION

PATENT NO. : 5,866,433
DATED : February 2, 1999
INVENTOR(S) : Schalkhammer et al.

It is certified that error appears in the above-indentified patent and that said Letters Patent is hereby corrected as shown below:

On the title page, [73] should read:

Assignee: Georg Bauer, Wien, Austria, part interest

Signed and Sealed this

Twenty-second Day of June, 1999

Attest:

Q. TODD DICKINSON

*Attesting Officer*     Acting Commissioner of Patents and Trademarks